United States Patent
Platteeuw et al.

(10) Patent No.: US 10,172,913 B2
(45) Date of Patent: *Jan. 8, 2019

(54) ORALLY DISINTEGRATING SOLID PHARMACEUTICAL DOSAGE UNIT CONTAINING A PARTUS CONTROL SUBSTANCE

(71) Applicant: Oxytone Bioscience B.V., Zeist (NL)

(72) Inventors: Johannes Jan Platteeuw, Boxtel (NL); Herman Jan Tijmen Coelingh Bennink, Zeist (NL)

(73) Assignee: Oxytone Bioscience B.V., Zeist (NL)

( * ) Notice: Subject to any disclaimer, the term of this patent is extended or adjusted under 35 U.S.C. 154(b) by 26 days.

This patent is subject to a terminal disclaimer.

(21) Appl. No.: 15/516,127

(22) PCT Filed: Sep. 29, 2015

(86) PCT No.: PCT/NL2015/050673
§ 371 (c)(1),
(2) Date: Mar. 31, 2017

(87) PCT Pub. No.: WO2016/053091
PCT Pub. Date: Apr. 7, 2016

(65) Prior Publication Data
US 2017/0304394 A1 Oct. 26, 2017

(30) Foreign Application Priority Data
Oct. 1, 2014 (EP) .................... 14187354

(51) Int. Cl.
| A61K 31/11 | (2006.01) |
| A61K 38/11 | (2006.01) |
| A61K 9/00 | (2006.01) |
| A61K 9/16 | (2006.01) |
| A61K 9/20 | (2006.01) |

(52) U.S. Cl.
CPC ............ *A61K 38/11* (2013.01); *A61K 9/006* (2013.01); *A61K 9/0056* (2013.01); *A61K 9/167* (2013.01); *A61K 9/1676* (2013.01); *A61K 9/205* (2013.01); *A61K 9/2013* (2013.01); *A61K 9/2018* (2013.01); *A61K 9/2054* (2013.01); *A61K 9/2077* (2013.01); *A61K 9/2095* (2013.01)

(58) Field of Classification Search
CPC ...... A61K 38/11; A61K 9/0056; A61K 9/006; A61K 9/205; A61K 38/08; A61K 9/167; A61K 9/1676; A61K 47/12; A61K 47/36; A61K 9/2013; A61K 9/2018; A61K 9/2054; A61K 9/2077; A61K 9/2095; A61K 47/186; A61K 47/48046; A61K 47/48853; A61K 47/48907
See application file for complete search history.

(56) References Cited

U.S. PATENT DOCUMENTS
8,920,819 B2 12/2014 Uchegbu et al.

FOREIGN PATENT DOCUMENTS

| AT | 251762 B | 1/1967 | |
| CN | 102580057 A | 7/2012 | |
| CN | 104055732 A | 9/2014 | |
| GB | 1 437 138 A | 5/1976 | |
| WO | WO-91/03233 A1 | 3/1991 | |
| WO | WO2004/026279 A1 * | 4/2004 | ............. A61K 9/00 |
| WO | WO-2004/026279 A1 | 4/2004 | |
| WO | WO2007/025249 A2 * | 3/2007 | ............. A61K 38/04 |
| WO | WO-2007/025249 A2 | 3/2007 | |
| WO | WO-2010/030180 A2 | 3/2010 | |
| WO | WO-2012/042371 A2 | 4/2012 | |

OTHER PUBLICATIONS

"Heat-stable oxytocin technology opportunity assessment prepared for the Merk for mothers program", Path, Mar. 2013, XP055173807, retrieved from the Internet: URL:http://sites.path.org/mnhtech/files/2013/03/HS1_18March2013.FINAL.pdf.

"Heat-stable sublingual oxytocin for the prevention and treatment of postpartum hemorrhage", Path, May 2014, XP055173819, retrieved from the Internet: URL: http://www.path.org/publications/files/TS_update_sublingual_oxytocin.pdf.

Ashigbie, "Background paper 6.16 postpartum haemorrhage", Priority Medicines for Europe and the World "A Public Health Approach to Innovation", Jan. 2013, XP055127881, retrieved from the Internet: URL:http://www.who.int/medicines/areas/priority_medicines/BP6_16PPH.pdf.

(Continued)

*Primary Examiner* — Audrea B Coniglio
(74) *Attorney, Agent, or Firm* — Gilberto M. Villacorta; Sunit Talapatra

(57) ABSTRACT

An orally disintegrating solid pharmaceutical dosage unit having a weight between 50 and 1,000 mg is disclosed. The dosage unit consists of: (a) 5-100 wt. % of coated particles comprising 50-99 wt. % of a core particle and 1-50 wt. % of a coating that envelops the core particle, said coating consisting of:

0.01-10 wt. % of a partus control substance selected from oxytocin, carbetocin, atosiban and combinations thereof;

5-50 wt. % of buffering agent;

15-80 wt. % of branched glucan;

0-78 wt. % of other pharmaceutically acceptable ingredients; and (b) 0-95 wt. % of one or more pharmaceutically acceptable excipients;

the solid dosage unit comprising at least 20 μg of the partus control substance and having a pH buffer range of 3.5-5.7.

17 Claims, No Drawings

(56) References Cited

OTHER PUBLICATIONS

De Groot et al., "Stability of oral oxytocics in tropical climates", World Health Organization, Ergot Task Group, 1994, 59 pages.

International Search Report issued in International Patent Application No. PCT/NL2015/050673, dated Feb. 16, 2016.

International Search Report issued in International Patent Application No. PCT/NL2015/050674, dated Feb. 16, 2016.

Metia et al., "In vitro and in vivo evaluation of a novel mucoadhesive buccal oxytocin tablet prepared with Dillenia indica fruit mucilage", Die Pharmazie, Apr. 2008, vol. 4, 270-274.

Sun et al., "Effect of dextran molecular weight on protein stabilization during freeze-drying and storage", CryoLetters, 2001, vol. 22, pp. 285-292.

Wang, Lyophilization and development of solid protein pharmaceuticals, International Journal of Pharmaceuticals, 2000, vol. 203, pp. 1-60.

Avanti et al., "A new strategy to stabilize oxytocin in aqueous solutions: I. The effects of divalent metal ions and citrate buffer", The AAPS Journal, Jun. 2011, vol. 13, No. 2, pp. 284-290.

Avanti et al., "Aspartate buffer and divalent metal ions affect oxytoxin in aqueous solution and protect it from degradation", Int. J. Pharm, Feb. 2013, vol. 444, pp. 139-145.

De Groot et al., "Bioavailability and pharmacokinetics of sublingual oxytocin in male volunteers", J. of Pharm. Pharmacol., 1995, vol. 47, pp. 571-575.

De Groot et al., "Oxytocin and desamino-oxytocin tablets are not stable under simulated tropical conditions", J. of Clinical Pharmacy and Therapeutics, 1995, vol. 20, pp. 115-119.

Hawe et al., "Towards heat-stable oxytocin formulations: analysis of degradation kinetics and identification of degradation products", Pharm. Res., Jul. 2009, vol. 26, No. 7, pp. 1679-1688.

\* cited by examiner

US 10,172,913 B2

ORALLY DISINTEGRATING SOLID PHARMACEUTICAL DOSAGE UNIT CONTAINING A PARTUS CONTROL SUBSTANCE

CROSS-REFERENCE TO RELATED APPLICATIONS

This application is the National Phase of International Patent Application No. PCT/NL2015/050673, filed Sep. 29, 2015, published on Apr. 7, 2016 as WO 2016/053091 A1, which claims priority to European Patent Application No. 14187354.7, filed Oct. 1, 2014. The contents of these applications are herein incorporated by reference in their entirety.

TECHNICAL FIELD OF THE INVENTION

The present invention provides an orally disintegrating solid pharmaceutical dosage unit having a weight between 50 and 1,000 mg, said dosage unit consisting of:
  5-100 wt. % of coated particles comprising 50-99 wt. % of a core particle and 1-50 wt. % of a coating that envelops the core particle, said coating consisting of:
    0.01-10 wt. % of a partus control substance selected from oxytocin, carbetocin, atosiban and combinations thereof;
    5-50 wt. % of buffering agent;
    15-80 wt. % of branched glucan;
    0-78 wt. % of other pharmaceutically acceptable ingredients;
  0-95 wt. % of one or more pharmaceutically acceptable excipients; the solid dosage unit comprising at least 20 μg of the partus control substance and having a pH buffer range of 3.5-5.7.

The solid dosage units of the present invention are particularly suited for sublingual, buccal or sublabial administration of the partus control substance.

The invention also provides the use of these solid dosage units in medical treatments, wherein the treatment comprises buccal, sublingual or sublabial adminstration of the solid dosage unit. The solid dosage unit is particularly suited for use in the treatment of postpartum haemorrhage.

BACKGROUND OF THE INVENTION

Oxytocin is a mammalian hormone, secreted by the posterior pituitary gland, that acts primarily as a neuromodulator in the brain. Oxytocin plays an important role in the neuroanatomy of intimacy, specifically during and after childbirth. It is released in large amounts after distension of the cervix and uterus during labour, facilitating childbirth, maternal bonding and lactation.

Oxytocin is a peptide of nine amino acids (a nonapeptide). Its systematic name is cysteine-tyrosine-isoleucine-glutamine-asparagine-cysteine-proline-leucine-glycine-amide. Its half-life in the blood is typically about three minutes. Oxytocin has a molecular mass of 1007.19 g/mol. One international unit (IU) of oxytocin is the equivalent of about 1.68 micrograms of pure peptide.

Oxytocin as a drug is often used to induce labour and support labour in case of non-progression of parturition and to treat obstetric haemorrhage. Obstetric haemorrhage is estimated to cause 25% of all maternal deaths and is the leading direct cause of maternal mortality worldwide. Postpartum haemorrhage (PPH), defined as vaginal bleeding in excess of 500 ml after delivery, accounts for most cases of obstetric hemorrhage. It occurs in more than 10% of all births and is associated with a 1% case fatality rate.

Although active management of the third stage of labour (AMTSL) can prevent up to 60% of PPH cases, PPH continues to have a devastating impact on women in low-resource settings where home births are common and health care facilities are often inaccessible. Obstetric hemorrhage accounts for 34% of maternal deaths in Africa, 31% in Asia, and 21% in Latin America and the Caribbean. Among women who do survive PPH, approximately 12% will have severe anemia. Also, women who survive severe PPH (greater than 1,000 ml of blood loss) are significantly more likely to die during the following year.

Injectable oxytocin (intravenously or intramuscularly) has been recommended by the World Health Organization (WHO) for routine use during AMTSL and is the preferred drug for the prevention and management of blood loss after childbirth. Administering the injection, however, requires skill, sterilized equipment, and proper disposal of medical waste. Oral administration of oxytocin is not a suitable route of administration, since the peptide oxytocin is degraded in the gastrointestinal tract.

At present, oxytocin is available only as a liquid formulation in single-dose vials of 10 IU for intramuscular (IM) or intravenous (IV) injection. Four other preparations under investigation are at various stages of development and introduction (Uterotonic Research and Policy Agenda for Reducing Mortality and Morbidity Related to Postpartum Haemorrhage. A consensus statement issued by the participants in the meeting on "The Role of Uterotonics in Reducing Postpartum Haemorrhage: What Next?", held on 4-5 Oct. 2011 in The Hague, The Netherlands). These preparations are:
a) oxytocin delivered IM via a Uniject® device packaged with a Time Temperature Indicator (TTI);
b) a more heat-stable liquid oxytocin formulation;
c) lyophilized heat-stable oxytocin reconstituted with sterile water for IM or IV injection;
d) a heat-stable powdered oxytocin formulation for aerosol delivery and inhalation.

In 1993 and 1994, WHO-supported studies demonstrated that oxytocin loses potency in field conditions, particularly tropical climates. Depending on the manufacturer and regulatory agency specification, all oxytocin products must be stored in either controlled room temperature (25° C. or lower) or refrigerated storage (2° C. to 8° C.) to ensure quality.

In third world countries, it is often practically and/or economically impossible to protect pharmaceutical preparations from the harmful effects of high temperatures and high humidity during transportation, storage and use. Besides stability in high temperature and humidity conditions, pharmaceutical preparations for use in tropical climates must fulfill extra requirements, such as a simple route of administration and untrained people should be able to administer the pharmaceutical preparation safely.

Carbetocin is a long-acting synthetic octapeptide having an action very similar to oxytocin. Carbotecin is also used as an obstetric drug to control postpartum haemorrhage and bleeding after giving birth. The commercially available carbetocin formulation PABAL® (100 μg/ml solution for injection, Ferring Pharmaceuticals Ltd.) is not stable at room temperature and requires refrigerated storage at a temperature of 2-8° C.

Atosiban is a synthetic nonapeptide and is an inhibitor of oxytocin and vasopressin. It is used as an intravenous medication as a labour repressor (tocolytic) to halt premature labour. Atosiban is available as a lyophilized (freeze dried) powder that should be stored desiccated below −18° C. At room temperature lyophilized atosiban is stable for 3 weeks.

Recently a lot a scientific research has been performed to study what causes the degradation of oxytocin in aqueous solutions.

Hawe et al. (Pharm Res. 2009 July; 26(7): 1679-1688) observed that the degradation of oxytocin strongly depends on the pH of the formulation, with the highest stability at pH 4.5.

Recent studies describe new strategies to stabilize oxytocin in aqueous solutions. Avanti et al. (The AAPS Journal. 2011; 13(2):284-290) and Avanti et al. (Int J Pharm. 2013 Feb. 28; 444(1-2):139-45) suggested that stability of oxytocin in aqueous solution can be improved by addition of divalent metal ions in combination with a citrate or aspartate buffer, respectively.

WO 2010/030180 mentions that the stability of aqueous peptide formulations, containing small therapeutic Cys-containing peptides such as oxytocin, is greatly enhanced by the presence of a buffer and at least one non-toxic source of divalent metal ions in a concentration of at least 2 mM.

WO 2012/042371 describes a pharmaceutical liquid composition, comprising carbetocin or pharmaceutically active salt thereof, and having pH between 5.0 and 6.0. This liquid composition may be stored at room temperature (e.g. at 25° C. and 60% relative humidity) for a sustained period (e.g. up to 2 years). The examples of the international patent application described liquid aqueous formulations containing carbetocine, buffer and anti-oxidant (methionine and/or EDTA).

A recently issued publication (http://path.org/publications/files/TS_oxytocin_fdt_for_pph_pos.pdf) describes a proposal for a project that aims to develop a heat-stable, fast-dissolving oxytocin tablet for sublingual administration. Several potential advantages of such a sublingual oxytocin tablet vis-á-vis existing oxytocin preparations for intramuscular injection or intravenous infusion are listed.

Sublingual tablets containing oxytocin have been marketed in the past (brand names Pitocin® and Syntocinon®). These products have been withdrawn from the market as greater control in induction and augmentation of labour could be achieved by intravenous or intramuscular administration of oxytocin. Sublingual administration was considered to be more unpredictable and in addition the pharmacokinetic profile showed an unfavourable latent period. Also, the sublingual tablets were not stable enough under tropical conditions.

De Groot et al. (J. of Pharm. Pharmacol. 1995, 47; 571-575) describe a study in which bioavailability and pharmacokinetics of sublingual oxytocin (Pitocin® tablet) was investigated. The study showed substantial inter-individual variability in bioavailability of oxytocin. The authors conclude that sublingual administration of oxytocin does not seem a reliable route for immediate prevention of PPH due to 'long' lag time and 'long' absorption half-life.

De Groot et al. (J. of Clinical Pharmacy and Therapeutics, 1995, 20, 115-119) describe experiments wherein the effect of simulated tropical conditions on buccal oxytocin tablets (tablet components not specified) was studied. The conclusion was that tropical conditions make oxytocin tablets unstable, with humidity as the most adverse factor. The oxytocin tablets were partially protected from the harmful effect of humidity by sealed aluminium package.

There remains a need for an oxytocin formulation for in-mouth (e.g. sublingual or buccal) administration that has good bioavailability and pharmacokinetics, that does not require refrigerated storage, that can be administered by untrained people and that can be manufactured and distributed at low cost. This same need exists for carbetocin and atosiban, especially since currently formulations for in-mouth administration of carbetocin or atosiban are not commercially available.

SUMMARY OF THE INVENTION

The present invention provides an orally disintegrating solid pharmaceutical dosage unit containing a partus control substance (PCS) that meets the aforementioned desiderata. More particularly, the present invention relates to an orally disintegrating solid pharmaceutical dosage unit having a weight between 50 and 1,000 mg, said dosage unit consisting of:

5-100 wt. % of coated particles comprising 50-99 wt. % of a core particle and 1-50 wt. % of a coating that envelops the core particle, said coating consisting of:
  0.01-10 wt. % of a partus control substance selected from oxytocin, carbetocin, atosiban and combinations thereof;
  5-50 wt. % of buffering agent;
  15-80 wt. % of branched glucan;
  0-78 wt. % of other pharmaceutically acceptable ingredients;
0-95 wt. % of one or more pharmaceutically acceptable excipients; the solid dosage unit comprising at least 20 µg of the partus control substance and having a pH buffer range of 3.5-5.7.

The solid dosage unit of the present invention is easy to manufacture and perfectly suited for sublingual, buccal or sublabial administration. Furthermore, the dosage unit does not need to be stored and distributed under temperature controlled conditions.

Another aspect of the invention relates to a method of preparing the aforementioned solid dosage unit, said method comprising the steps of:
  providing an aqueous solution comprising the PCS, the buffering agent, branched glucan and optionally one or more other pharmaceutically acceptable ingredients;
  combining the aqueous solution with carrier particles, to produce coated particles comprising a core particle and a coating containing the partus control substance, the buffering agent, the branched glucan and the optionally one or more other pharmaceutically acceptable ingredients;
  mixing the coated particles with the one or more pharmaceutically acceptable excipients; and
  forming the mixture into a solid dosage unit.

This preparation method offers the advantage that the aqueous solution can be dehydrated rapidly under controlled conditions. Thus, degradation of the PCS is effectively minimized and a homogenous coating layer is formed.

DETAILED DESCRIPTION OF THE INVENTION

A first aspect of the invention relates to an orally disintegrating solid pharmaceutical dosage unit having a weight between 50 and 1,000 mg, said dosage unit consisting of:
  5-100 wt. % of coated particles comprising 50-99 wt. % of a core particle and 1-50 wt. % of a coating that envelops the core particle, said coating consisting of:

0.01-10 wt. % of a partus control substance selected from oxytocin, carbetocin, atosiban and combinations thereof;

5-50 wt. % of buffering agent;

15-80 wt. % of branched glucan;

0-78 wt. % of other pharmaceutically acceptable ingredients;

0-95 wt. % of one or more pharmaceutically acceptable excipients; the solid dosage unit comprising at least 20 μg of the partus control substance and having a pH buffer range of 3.5-5.7.

The term 'partus control substance' as used herein refers to a pharmaceutical substance that is capable of repressing progression of partus, of inducing partus or of suppressing or preventing postpartum haemorrhage.

The term 'oxytocin' as used herein refers to oxytocin as well as pharmaceutically acceptable salts thereof.

The term 'carbetocin' as used herein refers to carbetocin as well as pharmaceutically acceptable salts thereof.

The term 'atosiban' as used herein refers to atosiban as well as pharmaceutically acceptable salts thereof.

The term 'buffering agent' as used herein refers to substances that can be used in aqueous systems to drive a solution to a certain pH (e.g. a pH within the range of 3.5-5.7) and that prevents a change in this pH. Buffering agents can be either the weak acid or weak base that would comprise a buffer solution (an aqueous solution comprising a mixture of a weak acid and its conjugate base or a weak base and its conjugate acid). Buffering agents are the substances that are responsible for the buffering seen in buffer solutions. Buffering agents are similar to buffer solutions in that buffering agents are the main components of buffer solutions. They both regulate the pH of a solution and resist changes in pH.

The term 'glucan' as used herein refers to a polysaccharide that is composed of repeating glucose units. The term 'glucan' encompasses both α-glucans and β-glucans. The term 'glucan' also encompassed glucans that have undergone partial hydrolysis.

The term 'branched glucan' as used herein refers to a glucan comprising a straight chain of glycosidically linked glucose molecules and branches of glycosidically linked glucose molecules that are linked to the aforementioned straight chain.

The term 'dextran' as used herein refers to a branched glucan with a straight chain of α-1,6 glycosidically linked glucose molecules and branches beginning from α-1,3 linkages. Dextran is synthesized from sucrose by certain lactic-acid bacteria, the best-known being *Leuconostoc mesenteroides* and *Streptococcus mutans*.

The term 'disulfide bond' as used herein, unless indicated otherwise, refers to a disulfide bond between two amino acid residues, for instance, a disulfide bond between two cystein residues.

The term 'medical treatment' as used herein encompasses both therapeutic and prophylactic treatment.

The term 'sublingual' as used herein refers to the pharmacological route of administration by which a pharmacologically active compound diffuses into the blood through tissues under the tongue.

The term 'buccal' as used herein refers to the pharmacological route of administration by which a pharmacologically active compound diffuses into the blood through tissues of the buccal vestibule, the area inside the mouth between the lining of cheek (the buccal mucosa) and the teeth/gums.

The term 'sublabial' as used herein refers to the pharmacological route of administration by which a pharmacologically active compound is placed between the lip and the gingiva and diffuses from there into the blood.

Examples of solid dosage units encompassed by the present invention include tablets, dragees, lozenges and films. In accordance with a preferred embodiment, the dosage unit is a tablet, most preferably a compressed tablet.

The solid dosage unit typically has a weight between 60 and 500 mg, more preferably between 70 and 300 mg, and most preferably between 75 and 200 mg.

The coated particles in the solid dosage unit preferably have a volume weighted average size between 10 and 400 μm, more preferably between 25 and 300 μm and most preferably between 50 and 250 μm.

The coated particles preferably represent 10-90 wt. %, more preferably 20-80 wt. % and most preferably 30-70 wt. % of the solid dosage unit, the remainder of the dosage unit consisting of one or more pharmaceutically acceptable excipients.

In accordance with one embodiment, the coated particles in the solid dosage unit contain 0.05-8 wt. %, more preferably 0.1-7 wt. %, even more preferably 0.2-6 wt. % and most preferably 0.3-5 wt. % of oxytocine, all percentages calculated by weight of the coating.

The solid dosage unit of the present invention typically contains oxytocin in an amount of 40-600 μg, more preferably 80-500 μg, even more preferably 100-450 μg and most preferably 150-400 μg.

In accordance with another embodiment, the coated particles in the solid dosage unit contain 0.2-10 wt. %, more preferably 0.5-9.5 wt. %, even more preferably 1-9 wt. % and most preferably 2-8.5 wt. % of carbetocine, all percentages calculated by weight of the coating.

The solid dosage unit of the present invention typically contains carbetocin in an amount of 100-5,000 μg, more preferably 200-4,000 μg, even more preferably 300-3,000 μg and most preferably 400-2,500 μg.

In a preferred embodiment the PCS is oxytocin. In another preferred embodiment the PCS is carbetocin. In another preferred embodiment the PCS is atosiban.

The core particle of the coated particles can be made of any pharmaceutically acceptable solid carrier material. Examples of suitable carrier materials include sugar alcohols, lactose, celluloses (including modified celluloses) and combinations thereof. Preferably, core particle contains at least 50 wt. %, more preferably at least 80 wt. % of a carrier material selected from mannitol, lactose, celluloses and combinations thereof.

According to a particularly preferred embodiment, the core particle contains at least 50 wt. %, more preferably at least 80 wt. % of a carrier material selected from mannitol, crystalline lactose, microcrystalline cellulose and combinations thereof.

The core particle that is present in the coated particles typically has a mass weighted average diameter of 8-350 μm, more preferably of 20-280 μm and most preferably of 40-240 μm.

The coated particles preferably comprise 60-98 wt. % of a core particle and 2-30 wt. % of the PCS-containnig coating. More preferably, the coated particles comprise 70-96 wt. % of a core particle and 4-20 wt. % of the PCS-containing coating. Most preferably, the coated particles comprise 5-15 wt. % of the PCS-containing coating.

Besides the coating containing the PCS, the coated particles may contain one or more additional coating layers, e.g an outer layer that covers the PCT-containing coating.

Typically, the one or more additional coating layers represent less than 40 w %., more preferably less than 30 wt. % and most preferably less than 20 wt. % of the coated particles.

The solid dosage unit preferably has a pH buffer range of 4.0 to 5.5, more preferably of 4.2 to 5.2. The pH buffer range of the solid dosage unit is determined by dispersing 1 g of the solid dosage unit in 10 ml of distilled water at 20° C. and measuring the pH after all soluble components of the dosage unit have dissolved in the water. The buffering agent is preferably contained in the coating in a concentration of 0.2-10 mmol/g, more preferably of 0.3-8 mmol/g and most preferably of 0.4-6 mmol/g.

In a preferred embodiment, the coating contains 6-30 wt. % of buffering agent, more preferably 7-25 wt. % and most preferably of 8-20 wt. % of buffering agent, all percentage calculated by weight of the coating.

The buffering agent in the coating preferably has a pH buffer range of 4.0 to 5.5, more preferably of 4.2 to 5.2. The pH buffer range of a buffering agent can be determined by dissolving 1 g of the buffering agent in 10 ml of distilled water at 20° C. and measuring the pH after all soluble components of the dosage unit have dissolved in the water.

The buffering agent in the coating is preferably selected from citrate, acetate, aspartate and combinations thereof. The term 'citrate', unless indicated otherwise, encompasses both fully protonated citric acid as well as salts of citric acid. The same holds, mutatis mutandis, for other buffering agents.

The branched glucan is preferably contained in the coating in a concentration of 20-70 wt. %, more preferably of 22-65 wt. % and most preferably of 24-60 wt. %, all percentage calculated by weight of the coating.

Examples of branched glucans that may be employed in accordance with the present invention include dextran, glycogen, amylopectin and combinations thereof. Preferably, the branched dextran employed is an α-glucan. Most preferably, the branched glucan employed is dextran.

In a particularly preferred embodiment the branched glucan is a hydrolyzed dextran. The hydrolyzed dextran has an average molecular weight between 10-2000 kDa, more preferably between 10-1000 kDa, even more preferably between 10-500 kDa and most preferably between 10-200 kDa.

Besides the PCS, the buffering agent and the branched glucan, the coating of the coated particles may optionally contain up to 70 wt. %, more preferably up to 65 wt. % and most preferably up to 60 wt. % of one or more other pharmaceutically acceptable ingredients, all percentages being calculated by weight of the coating.

The one or more other pharmaceutically acceptable ingredients that are optionally contained in the coating of the coated particles include a wide variety of pharmaceutically acceptable ingredients, such as divalent metal cations, polysaccharides (other than branched glucan), synthetic polymers (e.g. p polyvinylpyrrolidone, polyethylene glycol) proteins (e.g. gelatin), redox reagents, sequestrants, sugar alcohols, sugars and combinations thereof. The term 'polysaccharides' includes modified polysaccharides such as, for instance, hydroxypropylmethylcellulose and maltodextrin.

In accordance with a preferred embodiment, the coating contains 0.1-10 wt. % of divalent metal cation, more preferably 0.3-6 wt. % and most preferably of 0.5-4 wt. % of divalent metal cation, all percentage calculated by weight of the coating.

Preferably, the divalent metal cation and the PCS are present in the coating of the coated particles in a molar ratio between 1:1 and 1000:1, more preferably in a molar ratio between 2:1 and 300:1 and most preferably in a molar ratio between 4:1 and 100:1.

The divalent metal cation employed in the coating is preferably selected from $Mg^{2+}$, $Ca^{2+}$, $Cu^{2+}$, $Zn^{2+}$ and combinations thereof. More preferably, the divalent metal cation is selected from $Zn^{2+}$, $Ca^{2+}$ and combinations thereof. Most preferably, the divalent metal cation is $Zn^{2+}$.

The coating of the coated particles preferably contains 20-75 wt. %, more preferably 30-70 wt. % and most preferably 40-65 wt. %, calculated by weight of the coating, of a binder selected from hydroxypropylmethylcellulose (HPMC), polyvinylpyrrolidone, polyethylene glycol and combinations thereof. Most preferably the binder employed in the coating is HPMC.

In accordance with a preferred embodiment, the coating of the coated particles contain 0.01-10 wt. % of a sequestrant, more preferably contain 0.05-3 wt. % of sequestrant, most preferably contain 0.2-1.5 wt. % sequestrant, all percentages calculated by weight of the coating.

The sequestrant employed in the coating is preferably EDTA.

According to another preferred embodiment, the coating of the coated particles contain 0.01-10 wt. % of redox reagent. More preferably, said particles contain between 0.05-3 wt. % of redox reagent, most preferably between 0.2-1.5 wt. % of redox reagent, all percentages calculated by weight of the coating.

The redox reagent typically is a small molecule compound, with a molecular weight generally less than about 1000 g/mol, preferably less than about 500 g/mol.

In accordance with one embodiment, the redox agent is an oxidant that is capable of promoting the oxidative conversion of thiol groups into disulfide bonds. Examples of such oxidants include ascorbic acid, ascorbic acid derivatives (e.g. ascorbate esters), iodate, bromate and persulfate.

In accordance with another embodiment, the redox agent comprises at least one thiol (SH) functional group which can act as a reducing or oxidizing agent for disulfide bonds, thiols, or thiolate species present in the PCS and thereby moderate disulfide exchange reactions between peptides. Preferred examples include dithiothreitol, mercaptoethanol, cysteine, homocysteine, methionine, and glutathione (reduced).

Examples of pharmaceutically acceptable excipients that may be employed in the solid dosage unit of the present invention besides the coated particles include lactose, mannitol, xylitol, microcrystalline cellulose, croscarmellose sodium and combinations thereof.

The solid dosage units of the present invention can be packaged in different ways. Preferably, the dosage units are packaged in a blister pack containing at least 5 dosage units.

Another aspect of the invention relates to the use of the present dosage unit in medical treatment, wherein the treatment comprises buccal, sublingual or sublabial adminstration of said dosage unit. Preferably, the dosage unit is used in medical treatment of a mammal, most preferably a human.

According to a particularly preferred embodiment, the dosage unit contains at least 2 μg of oxytocin and is used in the treatment of postpartum haemorrhage, said treatment comprising buccal, sublingual or sublabial adminstration of said dosage unit. Even more preferably, the dosage unit is administered in an amount to provide at least 10 μg oxytocin, most preferably 15-400 μg oxytocin.

According to another preferred embodiment, the dosage unit contains at least 10 μg of carbetocin and is used in the treatment of postpartum haemorrhage, said treatment comprising buccal, sublingual or sublabial adminstration of said dosage unit. Even more preferably, the dosage unit is administered in an amount to provide at least 100 μg carbetocin, most preferably 200-2000 μg carbetocin.

According to yet another preferred embodiment, the dosage unit contains at least 5 μg, more preferably at least 10 μg of atosiban and is used to prevent or halt premature labour, said treatment comprising buccal, sublingual or sublabial adminstration of said dosage unit. Even more preferably, the dosage unit is administered in an amount to provide at least 100 μg atosiban, most preferably 1,000-75,000 μg atosiban.

Yet another aspect of the invention relates to a method of preparing a solid dosage unit as described above, said method comprising the steps of:
- providing an aqueous solution comprising the partus control substance, the buffering agent, branched glucan and optionally one or more other pharmaceutically acceptable ingredients;
- combining the aqueous solution with carrier particles, to produce coated particles comprising a core particle and a coating containing the partus control substance, the buffering agent, the branched glucan and the optionally one or more other pharmaceutically acceptable ingredients;
- mixing the coated particles with the one or more pharmaceutically acceptable excipients; and
- forming the mixture into a solid dosage unit.

Typically, the aqueous solution has a pH in the range of 3.5 to 5.7, more preferably in the range of 4.0 to 5.5 and most preferably in the range of 4.2 to 5.2 before the water removal.

The carrier particles can be made of any pharmaceutically acceptable solid carrier material. Examples of suitable carrier materials include sugar alcohols, lactose, celluloses and combinations thereof. Preferably, the carrier particles contain at least 50 wt. %, more preferably at least 80 wt. % of a carrier material selected from mannitol, lactose, celluloses (including modified celluloses) and combinations thereof.

The carrier particles employed in the present method typically have a mass weighted average diameter of 8-350 μm, more preferably of 20-280 μm and most preferably of 40-240 μm.

The optionally one or more other pharmaceutically acceptable ingredients that can be present in the aqueous solution are the same as the other pharmaceutically acceptable ingredients that can be present in the coating of the coated particles.

In a preferred embodiment, water is removed from the coating of the coated particles during or after the combining of the aqueous solution with the carrier particles.

The combining of the aqueous solution with the carrier particles and the removal of water preferably take place in a fluid bed dryer or a granulator. In a preferred embodiment, the granulator is operated under reduced pressure in order to facilitate removal of water by evaporation.

The one or more pharmaceutically acceptable excipients that are mixed with the coated particles before the forming of the mixture in a solid dosage unit are pharmaceutically acceptable excipients as defined herein before in relation to the solid dosage unit.

The forming of the mixture of coated particles and one or more pharmaceutically acceptable excipients into a solid dosage unit preferably comprises compaction of this mixture.

Compactibility is the ability of a powder bed to form a mechanically strong tablet; whereas the compressibility is the ability of a powder bed to be compressed and consequently be reduced in volume. Compaction as applicable to a pharmaceutical powder consists of the simultaneous processes of compression and consolidation of a two-phase (particulate solid-gas) system due to an applied force. Consolidation refers to the increase in the mechanical strength of a material as a result of particle/particle interactions.

The invention is further illustrated by the following non-limiting examples.

EXAMPLES

Example 1

An oxytocin containing coated powder was prepared by spraying an aqueous solution of oxytocin, citric acid, sodium citrate, zinc chloride, hydrolyzed dextran (Dextran 40) and hydroxypropylmethylcellulose (HPMC) onto mannitol powder in a fluid bed dryer. The spraying solution was prepared by adding the ingredients shown in Table 1 in the amounts indicated to 200 ml of distilled water and adjusting pH to 4.6 (using HCl or NaOH).

TABLE 1

| Ingredient | grams |
| --- | --- |
| Oxytocin | 0.25 |
| Citric acid anhydrate | 0.27 |
| Sodium citrate dehydrate | 0.80 |
| Zinc chloride | 0.27 |
| Dextran 40 | 2.5 |
| HPMC | 4.0 |

The mannitol powder used had a mass weighted average diameter of 200 μm. The (dry) composition of the dry coated mannitol powder obtained from the fluid bed dryer is shown in Table 2. Estimated water content of the coated powder was 2-3 wt. %.

TABLE 2

| Ingredient | Wt. % |
| --- | --- |
| Oxytocin | 0.16 |
| Citric acid | 0.17 |
| Sodium citrate | 0.51 |
| Zinc chloride | 0.17 |
| Dextran 40 | 1.58 |
| HPMC | 2.53 |
| Mannitol | 94.88 |

Next, the coated powder was combined with excipients (lactose, sodium starch glycolate, ascorbic acid, Ludiflash® and sodium stearyl fumarate) to produce the tablet formulation described in Table 3.

TABLE 3

| Ingredient | Wt. % |
| --- | --- |
| Coated powder | 45.46 |
| Lactose | 10.00 |
| Sodium starch glycolate | 5.00 |
| Ascorbic acid | 2.50 |
| Ludiflash ® | 35.54 |
| Sodium stearyl fumarate | 1.50 |

The aforementioned tablet formulation was compressed into tablets of 100 mg. Each tablet contained 73 μg (43.2 I.U.) of oxytocin. Both the coated powder and the tablets can be stored under ambient conditions for several months without a substantial decrease in oxytocin content being observed.

Example 2

Example 1 is repeated, except that this time more spraying solution is sprayed onto the mannitol powder The composition of the dry coated mannitol powder obtained from the fluid bed dryer is shown in Table 4.

TABLE 4

| Ingredient | Wt. % |
| --- | --- |
| Oxytocin | 0.37 |
| Citric acid | 0.39 |
| Sodium citrate | 1.18 |
| Zinc chloride | 0.39 |
| Dextran 40 | 3.65 |
| HPMC | 5.84 |
| Mannitol | 88.19 |

This coated oxytocin powder is combined with excipients (lactose, sodium starch glycolate, ascorbic acid, Ludiflash® and sodium stearyl fumarate) to produce the tablet formulation described in Table 5.

TABLE 5

| Ingredient | Wt. % |
| --- | --- |
| Coated powder | 45.46 |
| Lactose | 10.00 |
| Sodium starch glycolate | 5.00 |
| Ascorbic acid | 2.50 |
| Ludiflash ® | 35.54 |
| Sodium stearyl fumarate | 1.50 |

The aforementioned tablet formulation is compressed into tablets of 100 mg. Each tablet contains 0.17 mg (100 I.U.) of oxytocin.

Example 3

Example 1 is repeated, except that this time even more spraying solution is sprayed onto the mannitol powder than in Example 2.

The composition of the dry coated mannitol powder obtained from the fluid bed dryer is shown in Table 6.

TABLE 6

| Ingredient | Wt. % |
| --- | --- |
| Oxytocin | 0.73 |
| Citric acid | 0.77 |
| Sodium citrate | 2.35 |
| Zinc chloride | 0.79 |
| Dextran 40 | 7.31 |
| HPMC | 11.69 |
| Mannitol | 76.35 |

This coated oxytocin powder is combined with excipients (lactose, sodium starch glycolate, ascorbic acid, Ludiflash® and sodium stearyl fumarate) to produce the tablet formulation described in Table 7.

TABLE 7

| Ingredient | Wt. % |
| --- | --- |
| Coated powder | 45.46 |
| Lactose | 10.00 |
| Sodium starch glycolate | 5.00 |
| Ascorbic acid | 2.50 |
| Ludiflash ® | 35.54 |
| Sodium stearyl fumarate | 1.50 |

The aforementioned tablet formulation is compressed into tablets of 100 mg. Each tablet contains 0.33 mg (200 I.U.) of oxytocin.

Example 4

Oxytocin containing coated powders were prepared by spraying 4 different aqueous solutions of oxytocin, citric acid, sodium citrate, zinc chloride and branched glucan onto mannitol powder in a high shear granulator, followed by drying at 40° C. Four different branched glucans were tested, i.e. Dextran 20, Dextran 40, Dextran 60 and pregelatinised starch. The spraying solutions were prepared by adding the aforementioned ingredients to demineralized water and adjusting pH to 4.6 (using HCl or NaOH). The mannitol powder used had a mass weighted average diameter of 100 µm.

Next, the coated powders (water content appr. <1% wt. %). were combined with excipients (lactose, sodium starch glycolate, ascorbic acid, Ludiflash® and mangnesium stearate) to produce the tablet formulations (dry weight) shown in Table 8.

TABLE 8

| | Parts by weight | | | |
| --- | --- | --- | --- | --- |
| | 1 | 2 | 3 | 4 |
| Granulate | | | | |
| Oxytocin | 0.33 | 0.33 | 0.33 | 0.33 |
| Citric acid anhydrate | 0.33 | 0.33 | 0.33 | 0.33 |
| Trisodium citrate dihydrate | 1.00 | 1.00 | 1.00 | 1.00 |
| Zinc chloride | 0.35 | 0.35 | 0.35 | 0.35 |
| Dextran 40 | 3.30 | | | |
| Pregelatinised starch [1] | | 3.32 | | |
| Dextran 20 | | | 3.29 | |
| Dextran 60 | | | | 3.31 |
| Mannitol | 44.61 | 44.68 | 44.72 | 44.71 |
| Tablet | | | | |
| Granulate | 49.93 | 50.03 | 50.05 | 50.05 |
| Lactose monohydrate | 9.99 | 10.03 | 9.98 | 10.05 |
| Sodium starch glycolate | 5.03 | 5.03 | 5.01 | 4.96 |
| Ludiflash ® | 33.99 | 33.91 | 33.97 | 33.94 |
| Magnesium stearate | 1.07 | 1.00 | 1.00 | 1.00 |
| Total | 100.00 | 100.00 | 100.00 | 100.00 |

[1] Starch 1500 ®, ex Colorcon (a mix of corn starch and pregelatinized starch, comprising 73% amylopectin and 27% amylase).

The aforementioned tablet formulations were compressed into tablets of 100 mg. Each tablet contained 333 µg (200 I.U.) of oxytocin.

Stability of these tablets was investigated by storing these tablets in alu-sachets at 40° C. and a relative humidity of 75%. After 6 months storage under these conditions oxytocine content of the 4 tested tablets had decreased by not more than a few percent.

Example 5

Granulate number 1 of Example 4 was used to prepare tablets from 4 different tablet formulations. The compositions of these tablet formulations are shown in Table 9.

TABLE 9

|  | parts by weight | | | |
| --- | --- | --- | --- | --- |
|  | 1 | 2 | 3 | 4 |
| Oxytocine granulate | 49.92 | 50.00 | 50.00 | 50.02 |
| Lactose monohydrate | 10.08 | 10.05 |  | 9.94 |
| Croscarmellose sodium | 4.99 | 5.02 | 5.00 | 5.05 |
| Amorphous silica [1] |  |  |  | 2.03 |
| Ludiflash ® | 34.01 |  |  |  |
| Mannitol |  | 33.33 | 41.99 |  |
| Prolsolv ODT [2] |  |  |  | 33.99 |
| Magnesium stearate | 1.00 | 1.00 | 1.00 | 1.00 |
| Total | 100.00 | 100.00 | 100.00 | 100.00 |

[1] Silica AL-1 FP (ex W.R Grace & Co.)
[2] Ex JRS Pharma (microcrystalline cellulose, colloidal silicon dioxide, mannitol, fructose, crospovidone)

These tablet formulations were compressed into tablets of 100 mg. Each tablet contained 333 μg (200 I.U.) of oxytocin.

Stability of these tablets was investigated by storing these tablets in Alu-sachets at 40° C. and a relative humidity of 75%. After 6 months storage under these conditions oxytocine content of the 4 tested tablets had decreased by not more than about 10 percent.

Example 6

200 ml stock solutions were prepared on the basis of the formulation shown in Table 1. The water used was at room temperature (appr. 20° C.) The solid ingredients, except for the oxytocin, were introduced into a container. Approximately 90% of the required water was added, followed by continuous stirring with a magnetic stirrer until all solids were dissolved. Oxytocin was added and the pH of the solution was set with 1M HCl or 1M NaOH to the required pH value (see Table 1). The remaining amount of water was added and mixed. The solution was stored at 2-8° C.

TABLE 10

| Ingredients | |
| --- | --- |
| Citric acid anhydrate | 0.265 g |
| Sodium citrate dihydrate | 0.805 g |
| EDTA | 0.200 g |
| Oxytocin | 0.022 g |
| HCl | qs |
| NaOH | qs |
| Purified water | 200 ml |
| pH | 5.2 |

Solutions were prepared by adding additional ingredients (see Table 11) to 20 ml of the stock solution (at room temperature). The solutions were stirred until all solids were dissolved. After addition of the ingredients the pH was measured (Table 11).

TABLE 11

| Solution | Ingredient (g) | pH |
| --- | --- | --- |
| 1 | 1 g mannitol | 5.23 |
| 2 | 1 g sucrose + 0.4 g raffinose | 5.24 |
| 3 | 1 g dextran 40 | 5.28 |

10 ml samples of these solutions were freeze dried overnight using a benchtop freeze drier. The freeze dried powder was stored at 2-8° C. In addition, 10 ml samples of these solutions were stored at 2-8° C.

After preparation of all samples, the samples were transferred to accelerated stability testing conditions (40° C./75% RH). The oxytocin concentration was determined in samples taken at the start of the stability testing (t=0) and 1 month later. For sample 3 the oxytocin concentration was also measured after 2 months of accelerated stability testing. The results of these analyses are shown in Table 12.

TABLE 12

|  | Solution Oxytocin % [1] | | Powder Oxytocin % [1] | |
| --- | --- | --- | --- | --- |
| Sample | 1 month | 2 months | 1 month | 2 months |
| 1 | 56.7 | — | 83.5 | — |
| 2 | 57.0 | — | 80.3 | — |
| 3 | 48.4 | 26.9 | 99.4 | 101.1 |

[1] Concentration calculated as percentage of oxytocin in sample t = 0

The invention claimed is:

1. An orally disintegrating solid pharmaceutical dosage unit having a weight between 50 and 1,000 mg and comprising:
   (a) 5-100 wt. % of coated particles comprising 50-99 wt. % of a core particle and 1-50 wt. % of a coating that envelops the core particle, the coating comprising:
      (i) 0.01-10 wt. % of a partus control substance selected from oxytocin, carbetocin, atosiban and combinations thereof;
      (ii) 5-50 wt. % of buffering agent;
      (iii) 15-80 wt. % of branched glucan;
      (iv) 0-78 wt. % of other pharmaceutically acceptable ingredients;
   (b) 0-95 wt. % of one or more pharmaceutically acceptable excipients;
   wherein the solid dosage unit comprises at least 20 μg of the partus control substance and has a pH buffer range of 3.5-5.7, determined by dispersing 1 g of the solid dosage unit in 10 ml of distilled water at 20° C. and measuring the pH after all soluble components of the dosage unit have dissolved in the water.

2. The dosage unit according to claim 1, wherein the buffering agent has a pH buffer range of 4.0 to 5.5.

3. The dosage unit according to claim 1, wherein the buffering agent is selected from citrate, acetate, aspartate and combinations thereof.

4. The dosage unit according to claim 1, wherein the branched glucan is hydrolyzed dextran with an average molecular weight in the range of 10-200 kDa.

5. The dosage unit according to claim 1, wherein the partus control substance is oxytocin.

6. The dosage unit according to claim 1, wherein the partus control substance is carbetocin.

7. The dosage unit according to claim 1, wherein the partus control substance is atosiban.

8. The dosage unit according to claim 1, wherein the coating contains 0.02-10 wt. % of divalent metal cation.

9. The dosage unit according to claim 8, wherein the divalent metal cation and the partus control substance are present in the coating in a molar ratio between 5:1 and 1000:1.

10. The dosage unit according to claim 9, wherein the divalent metal cation and the partus control substance are present in the coating in a molar ratio between 10:1 and 300:1.

11. The dosage unit according to claim 1, wherein the core particle comprises at least 50 wt. % of a carrier material selected from mannitol, lactose, celluloses and combinations thereof.

12. The dosage unit according to claim 1, wherein the core particle comprises at least 80 wt. % of a carrier material selected from mannitol, lactose, celluloses and combinations thereof.

13. The dosage unit according to claim 1, wherein the one or more pharmaceutically acceptable excipients are selected from lactose, mannitol, xylitol, microcrystalline cellulose, croscarmellose sodium and combinations thereof.

14. A method of medical treatment, comprising buccally, sublingually or sublabially administering a dosage unit according to claim 1.

15. The method according to claim 14, wherein the treatment is for postpartum haemorrhage, and the partus control substance is selected from oxytocin, carbetocin and combinations thereof.

16. The method according to claim 12, wherein the treatment is to prevent or halt premature labour, and the dosage unit comprises atosiban.

17. A method of preparing a solid dosage unit according to claim 1, comprising:
(a) providing an aqueous solution comprising the partus control substance, the buffering agent, branched glucan and optionally one or more other pharmaceutically acceptable ingredients;
(b) combining the aqueous solution with carrier particles, to produce coated particles comprising a core particle and a coating containing the partus control substance, the buffering agent, the branched glucan and the optional one or more other pharmaceutically acceptable ingredients;
(c) mixing the coated particles with the one or more pharmaceutically acceptable excipients; and
(d) forming the mixture into a solid dosage unit.

* * * * *